(12) United States Patent
Canali et al.

(10) Patent No.: US 8,827,716 B2
(45) Date of Patent: Sep. 9, 2014

(54) METHOD AND DEVICE FOR AUTOMATION OF THE INTERPRETATIVE ANALYSIS OF A DIGITAL LINE DRAWN BY A PERSON

(75) Inventors: Mario Canali, Milan (IT); Giovanni Cino, Carnate (IT)

(73) Assignee: Mario Canali, Milan (IT)

(*) Notice: Subject to any disclaimer, the term of this patent is extended or adjusted under 35 U.S.C. 154(b) by 1 day.

(21) Appl. No.: 13/577,024

(22) PCT Filed: Jan. 28, 2011

(86) PCT No.: PCT/EP2011/051204
§ 371 (c)(1),
(2), (4) Date: Aug. 3, 2012

(87) PCT Pub. No.: WO2011/095437
PCT Pub. Date: Aug. 11, 2011

(65) Prior Publication Data
US 2012/0308974 A1    Dec. 6, 2012

(30) Foreign Application Priority Data
Feb. 3, 2010 (IT) .............................. MI2010A0155

(51) Int. Cl.
*G09B 19/00* (2006.01)
*A61B 5/00* (2006.01)
*A61B 5/16* (2006.01)

(52) U.S. Cl.
CPC ................. *A61B 5/16* (2013.01); *A61B 5/7267* (2013.01); *A61B 85/167* (2013.01)
USPC .......................................... 434/236; 434/155

(58) Field of Classification Search
USPC ............ 434/236, 155; 600/300; 382/119, 187
See application file for complete search history.

(56) References Cited

U.S. PATENT DOCUMENTS

| 6,454,706 | B1 | 9/2002 | Pullman |
| 7,636,457 | B2 | 12/2009 | Franke et al. |
| 2009/0191524 | A1* | 7/2009 | Kim .............................. 434/236 |

FOREIGN PATENT DOCUMENTS

| WO | 2005072611 A1 | 8/2005 |
| WO | 2009139008 A1 | 11/2009 |

OTHER PUBLICATIONS

Mutalib, et al.; "Personality Analysis Based on Letter "t" Using Back Propagation Neural Network"; Proceedings of the International Conference on Electrical Engineering and Informatics Institut Teknologi Bandung, Indonesia, Jun. 2007, pp. 496-499; ISN: 978-979-16338-0-2; URL:http://repository.gunadarma.ac.id:8000/703/1/B-102.pdf>.

International Search Report and Written Opinion dated Mar. 29, 2011 from PCT/EP2011/051204.

* cited by examiner

*Primary Examiner* — Timothy A Musselman
(74) *Attorney, Agent, or Firm* — Ohlandt, Greeley, Ruggiero & Perle, L.L.P.

(57) ABSTRACT

The method for the automation of the interpretative analysis of a digital line drawn by a person is provided. The method includes a preliminary step for the acquisition of an archive of digital lines drawn by persons; a preliminary step for the acquisition of graphic evaluations of each of the lines of the archive; a preliminary step for the acquisition of psychological evaluations of the persons who have drawn each of the lines of the archive. The method further includes a preliminary step of providing a first and/or at least a second supervised neural network and relative training to associate, for each of the lines of the archive, the graphic evaluations with the corresponding psychological evaluations. The method further includes a step for the acquisition of a new digital line drawn by a person for the execution of its interpretative analysis; a step for the acquisition of the graphic evaluations for the new line; and an association step wherein the first and/or second trained supervised neural network automatically associates the corresponding psychological evaluations with the graphic evaluations of the new line.

13 Claims, 9 Drawing Sheets

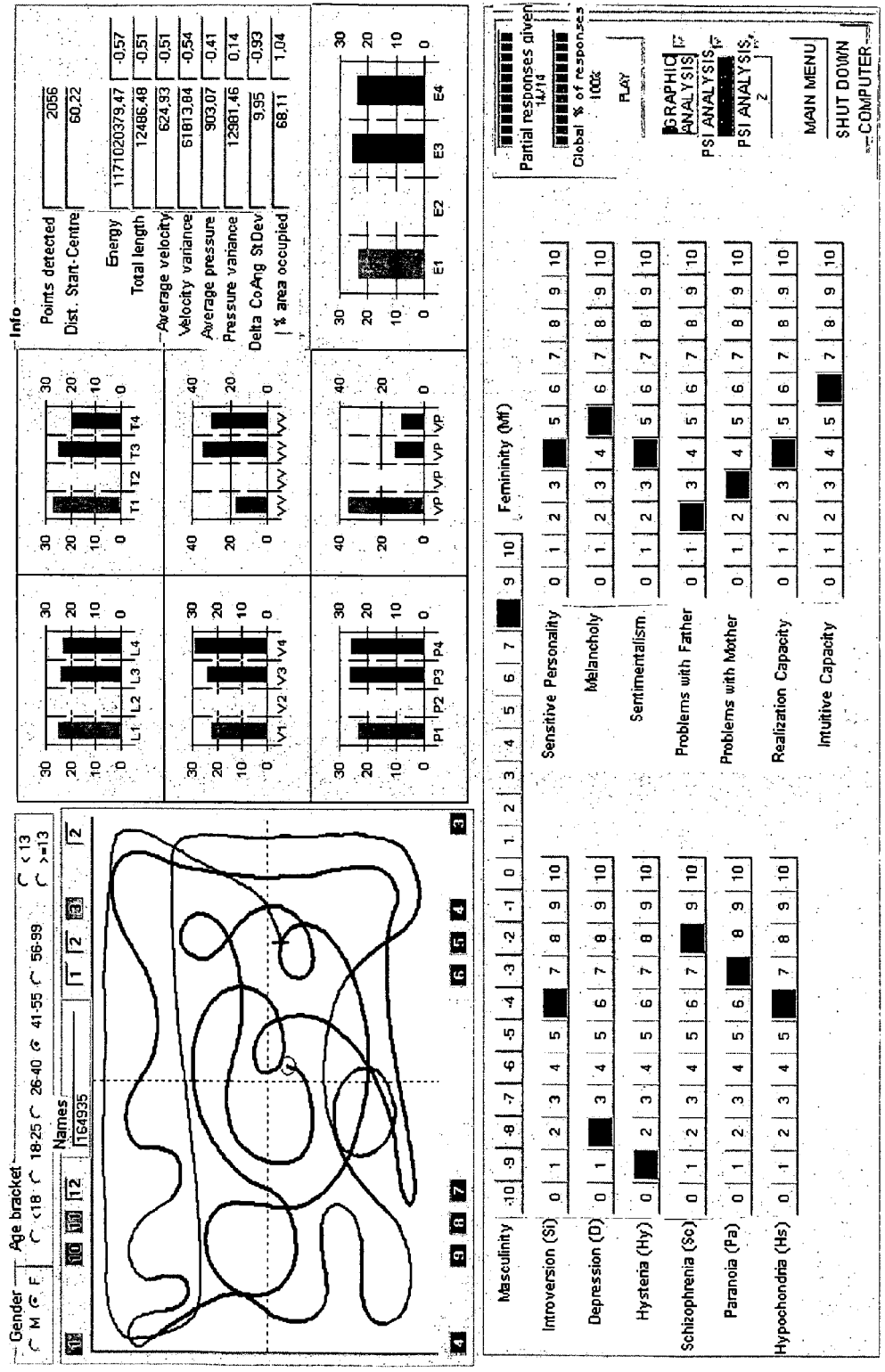
Fig. 6 (FIRST PART)

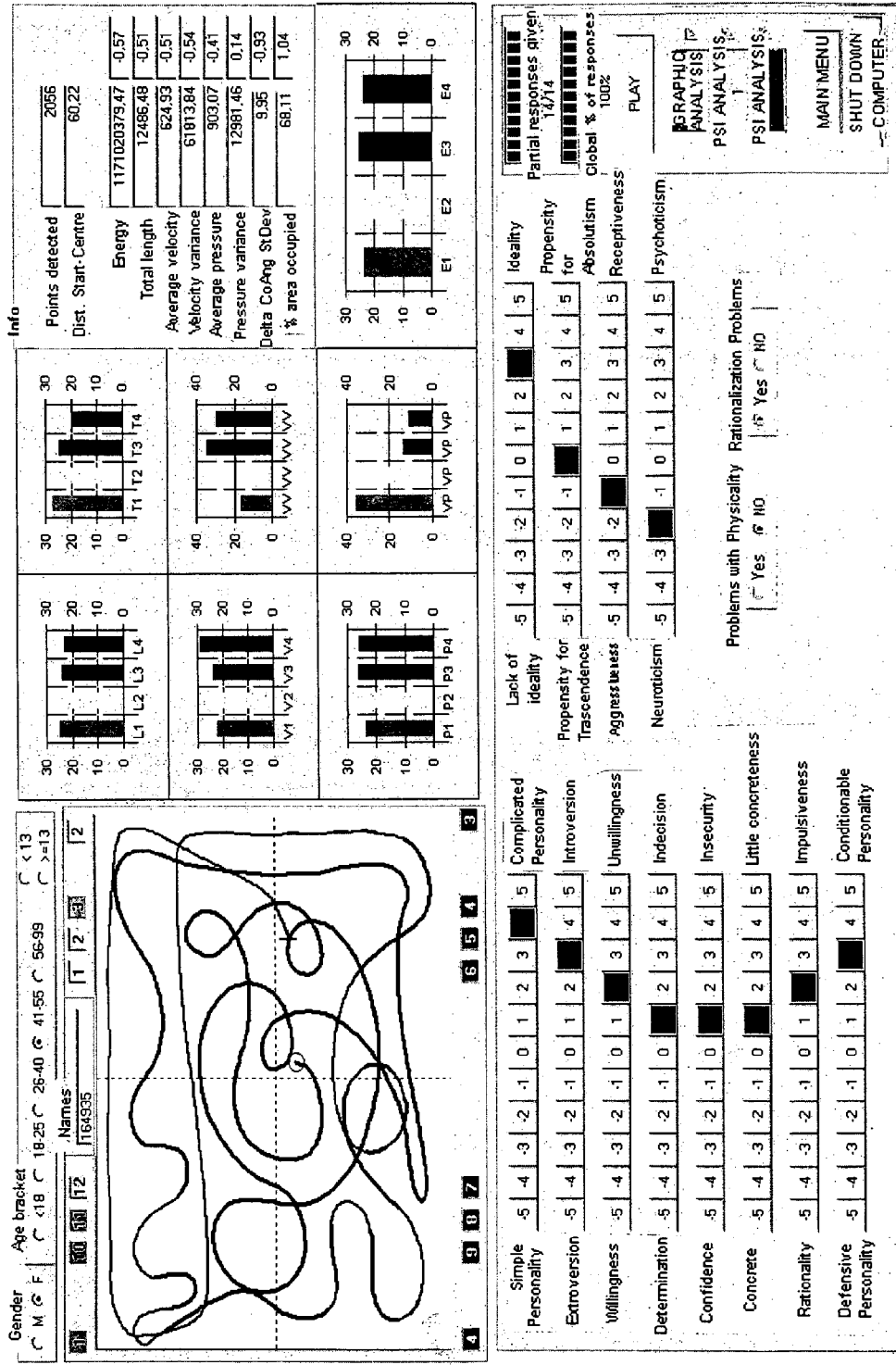
Fig. 6 (SECOND PART)

METHOD AND DEVICE FOR AUTOMATION OF THE INTERPRETATIVE ANALYSIS OF A DIGITAL LINE DRAWN BY A PERSON

The present invention relates to a method and a device for automation of the interpretative analysis of a digital line drawn by a person.

The actual situation, for the troublesome spreading of physical suffering, the diffuse need in every field, personal and familiar, educational, working and social, to evaluate attitudes, inclinations and physical disorders, requires the availability of a test of easy administration, with operating and evaluating times the shortest as possible, which is safe in its inner logic and coherence, and permits the punctual control of the procedures, the comparison with other tests, the possibility of improvements and research, and which is able to meet the lack of judgment by an expert.

The use of digital instruments applied to the administration and evaluation of psychological tests is now a consolidated practice.

The pursued automation relates to the proposition of the deliveries, the acquisition of the answers to questions, the calculations for elaborating an evaluation score, the statistical analyses for analysing the collected data.

These automations have greatly improved the times needed for the execution of the tests, eliminating the possibility of errors due to the execution of the needed calculations, facilitating the standardization of the procedures of administration and evaluation, by rendering less intrusive the presence of an examiner which inevitably conditions the execution of the tests.

In any case, the known attempts for the automation of the tests based on the answer to a series of questions, although reducing the execution times by means of the request of a simple selection among conveniently preset answers, cannot reduce beyond a determined limit the list of the answers and therefore the times needed to read and understand them, and to indicate an answer.

Other issues are present in the attempts of automation of the tests for the analysis of the execution of manually drawn signs.

The relation between manually drawn signs (in writing and drawing) and the psychological profile of the person have been subjected to a study and a practice since a long time.

In this case also, the availability of digital instruments able to precisely register the execution of drawings traced with a stylus on an appropriate digital medium, has permitted to accurately register and measure both the dynamics and the graphic result of the drawing.

In any case, it is very controversial the fact that a purely quantitative, numeric and statistic analysis of the drawing be able to permit an attribution of psychological judgments.

Therefore it is still deemed necessary to use both the formal analysis (rectilinear and curvilinear trends, presence of peaks, spirals, empty or filled spaces, and so on) and the qualitative analysis (harmony, disharmony, equilibrium, softness, and so on). But the formal/qualitative analysis at the moment is done in an exhaustive way only by physical persons (experts). This creates further issues: if on one side you don't want to miss out the richness of the judgment of an expert person, on the other side it is extremely difficult to objectively assess the criteria for defining this kind of classes and also of the criteria for attributing lines executed by the individuals to these classes.

The need of always having the physical presence of an expert person at disposal, limits in fact the utilization of the test.

The same kind of difficulty is found in the automatic attribution of psychological evaluations to the graphic evaluations.

The technical task of the present invention is therefore to provide a method and a device for the automation of the interpretative analysis of a digital line drawn by a person, which permit to eliminate the technical drawbacks lamented in the known art.

Within this technical task, a scope of the invention is to realize a method and a device for the automation of the interpretative analysis of a digital line drawn by a person which be able to eliminate the need of the presence of an expert.

Said technical task, and also these and other scopes according to the present invention are reached by realizing a method for automation of the interpretative analysis of a digital line drawn by a person on a digital electronic medium, characterized in that it comprises:

a preliminary step for the acquisition of an archive of digital lines drawn by a plurality of persons;

a preliminary step for the acquisition of graphic evaluations of each of said lines of said archive;

a preliminary step for the acquisition of psychological evaluations of the persons who have drawn each of said lines of said archive;

a preliminary step of providing a first and/or at least a second supervised neural network and relative training to associate, for each of said lines of said archive, the graphic evaluations with the corresponding psychological evaluations;

a step for the acquisition, through said digital medium, of a new digital line drawn by a person for the execution of its interpretative analysis;

a step for the acquisition of the graphic evaluations of said new line; and an association step wherein said first and/or second trained supervised neural network automatically associates the corresponding psychological evaluations with the graphic evaluations of said new line.

In the preliminary step for the acquisition of the psychological evaluations, these are established by an expert who evaluates according to psychological criteria each line in the archive or they are acquired through the performance of every kind of test administered to every person who has executed the line.

Preferably, said first supervised neural network is trained to associate the graphic evaluations of each of said lines of said archive with psychological evaluations deriving from the analysis of each of said lines by said expert.

Preferably, said second supervised neural network is trained to associate the graphic evaluations of each of said lines of said archive with psychological evaluations deriving from another test.

Preferably, an execution step of the psychological evaluation is provided, both by said first supervised neural network and by said second supervised neural network when said new line is drawn on said digital electronic medium.

Preferably, said graphic evaluations of each of said lines of said archive comprise at least quantitative graphic evaluations established by an electronic processor interacting with said digital electronic medium and formal/qualitative graphic evaluations.

Preferably, said formal/qualitative graphic evaluations of each of said lines of said archive in said preliminary step for the acquisition of graphic evaluations comprise also first formal/qualitative graphic evaluations established by an expert.

Preferably, said formal/qualitative graphic evaluations of each of said lines of said archive in said preliminary step for the acquisition of graphic evaluations comprise at least second formal/qualitative evaluations based on the belonging of each line of the archive to classes self-generated by at least a non-supervised neural network conveniently provided to classify the lines based on formal/qualitative graphic characteristics deemed to be significant.

Preferably, said method comprises also a preliminary step of providing a third supervised neural network and relative training to associate to each of said lines of said archive the corresponding first formal/qualitative graphic evaluations according to the modes of the expert.

Said third trained supervised neural network automatically associates the corresponding first formal/qualitative graphic evaluations with each of said new lines.

Within the scope of the present invention there is also a method in which the presence of the third supervised neural network is not foreseen. In such a case, in the analysis of a new line, to the first trained neural supervised network only the quantitative graphic evaluations and the second formal/qualitative evaluations of the non-supervised network are presented and inputted, by exploiting the intrinsic characteristics of the fault tolerance of the neural networks.

Preferably, said method comprises also a preliminary step of providing extraction systems from said first and second trained supervised neural networks of the general rules of associating the psychological evaluations to graphic evaluations, so permitting to describe the knowledge acquired by the supervised neural networks.

The quantitative graphic evaluations refer to quantitative characteristics comprising at least geometric, physical and statistical parameters of said lines.

Said physical parameters of said quantitative characteristics comprise, for each point detected during the drawing, at least the spatial position thereof on the sensitive area of the digital electronic medium, the instant in which it was performed and preferably the pressure with which it was performed.

Said invention provides a device for the execution of the above cited method, comprising an electronic processor interacting with the digital electronic medium, preferably formed by a graphics tablet or a touchscreen.

Further characteristics and advantages of the invention will be more evident from the description of a preferred but not exclusive embodiment of said method and device for the automation of the interpretative analysis of a digital line drawn by a person, illustrated in an indicative and not limiting way in the annexed drawings, in which:

FIG. 6 shows the interface of the electronic processor which is presented to the expert for the psychological evaluations of said lines in the preliminary step for the acquisition of the psychological evaluations of each of said lines;

Figure 1:
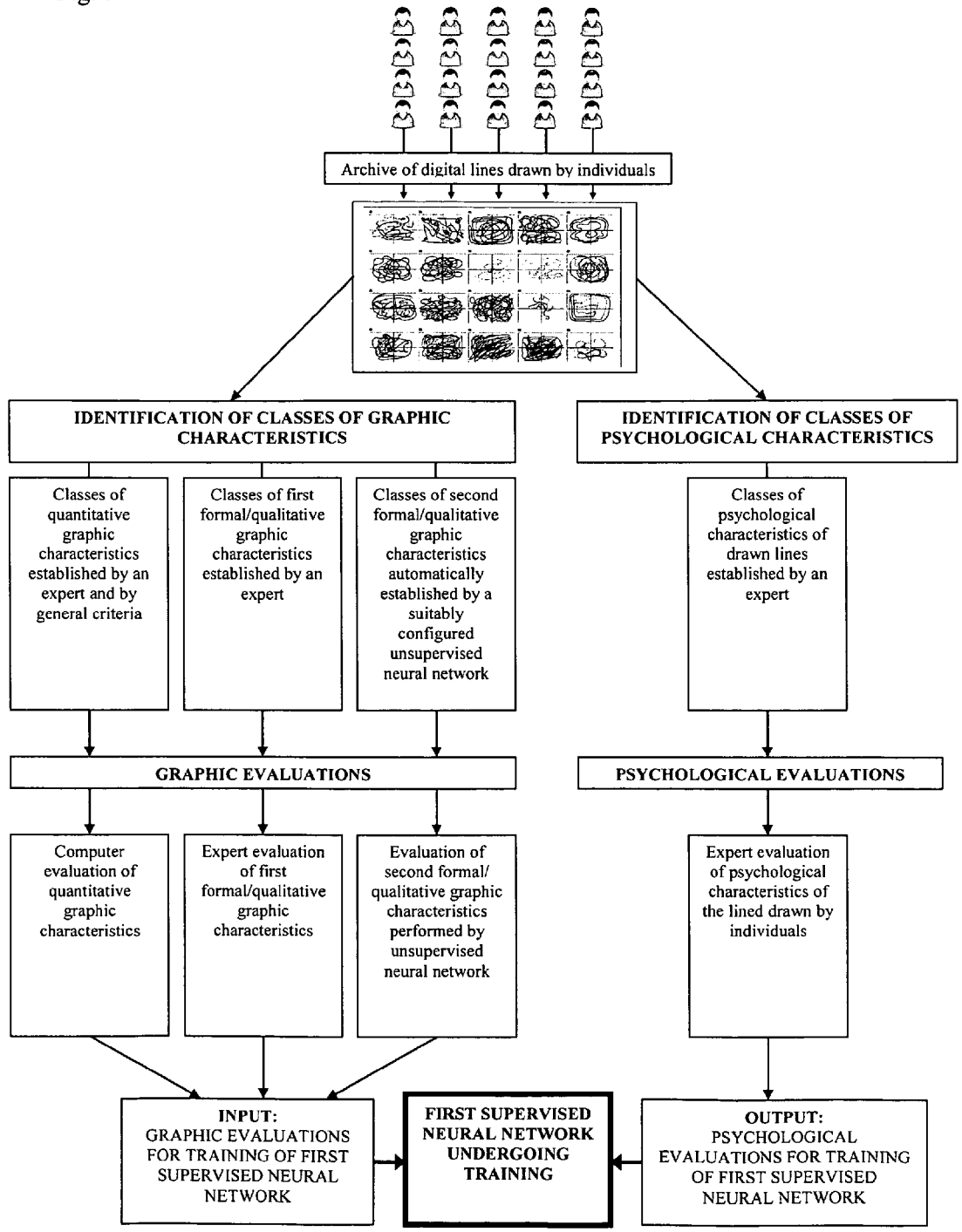
FIG. 1 shows a diagram with the training procedure of the first supervised neural network for the association of the graphic evaluations of said lines to psychological evaluations of said lines provided by the expert.
Figure 2:
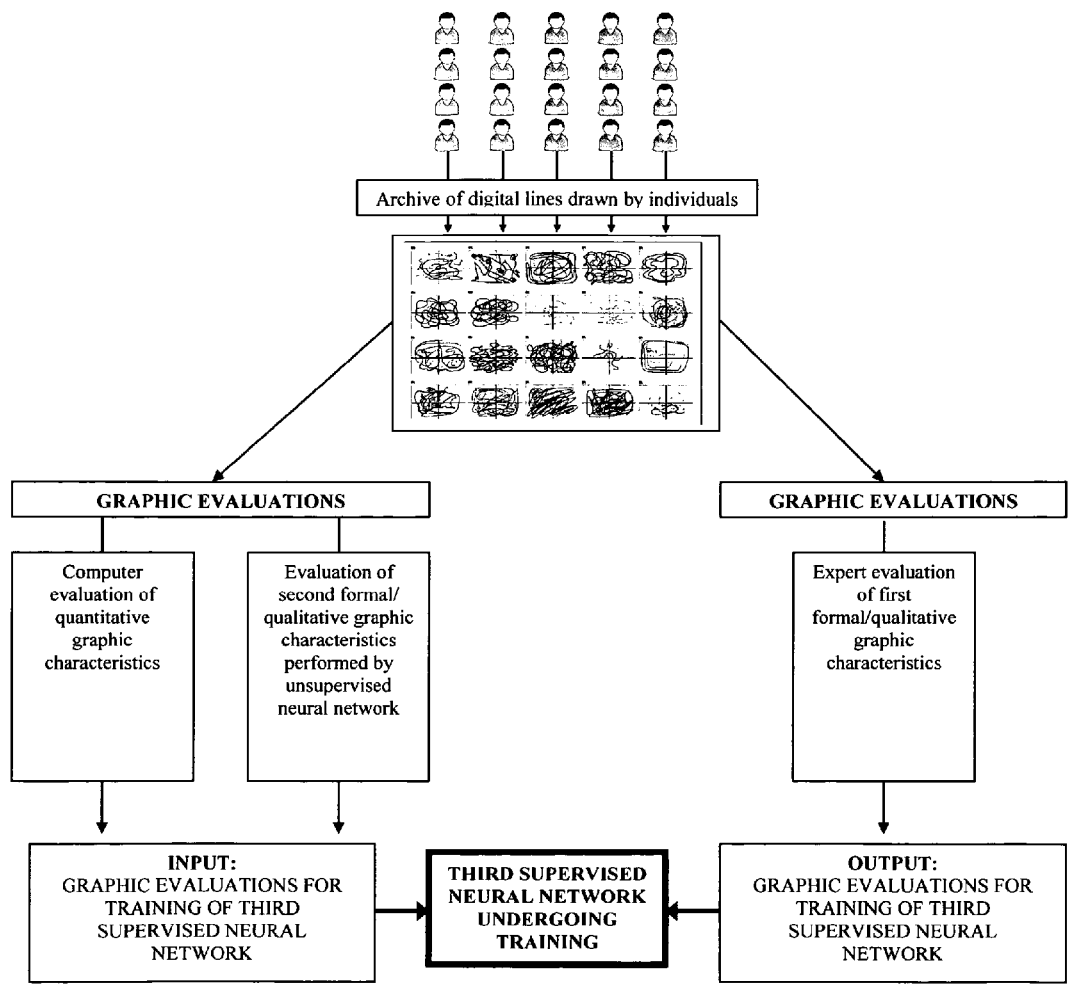
FIG. 2 shows a diagram with the training procedure of the third supervised neural network.

With reference to cited figures, the method for the automation of the interpretative analysis of a digital line drawn by a person requires a device comprising an electronic processor able to interact with a digital electronic medium for the detection of said digital line.

Said digital electronic medium is preferably a graphics tablet or also a touchscreen, used by means of a stylus or directly free-hand.

The delivery of the test to said person preferably requires the drawing onto the sensitive area of the digital medium of a continuous line, that is, realized for a determined time without detachment from the sensitive area. Said line must be preferably a scribble. In such a case the acquisition of the drawn line is validated for its next analysis only when it does not have an apparent meaning.

Psychology has always nurtured a great interest for scribbles, as it considers that a scribble, just for its execution modes non destined to an end but only to be drawn often unconsciously, can be referred to the internal psychological dynamics of said person.

It is considered that said scribble, drawn notwithstanding the manifest intention of not wanting to say anything, is finally a faithful mirror of the personality of who executes it.

Of said scribble the dynamics are investigated with which it is executed, and the result of such dynamics is interpreted as a drawing.

As a drawing it is investigated in its formal/qualitative aspects, in the development modes of the sign, in the configurations that it evidences when disposing itself spatially.

The graphic characteristics are finally interpreted as a map of the personality, and are as such evaluated.

The scribble reduces in a significant way eventual interferences due to differences in culture, training and drawing ability, rendering the task easily accessible to anybody and not boring.

The standardization of the modes of execution of the scribble permits to execute calculations on homogeneous data, permitting comparisons and statistics.

The digital electronic medium permits to precisely set the standard execution modes of a scribble, particularly with uniformity in the administration mode and uniformity in the time permitted for the execution.

The execution time, indicated by the expert as adequate in order to obtain psychologically significant drawings, can be easily set and controlled by the electronic processor.

The execution time of the test becomes extremely confined in comparison with other tests, particularly when compared with the tests of answers to a series of questions and with projective tests today used.

With an electronic processor also the precise and constant area of the digital support con be indicated and controlled, wherein the drawing can be traced, and the eventual interruption during the execution can be intercepted automatically, by obliging whom who executes the test to repeat it without interruptions, so adding another element of uniformity.

The further condition, indicated by the expert and present at the delivery, of drawing the line without executing any kind of figuration, permits to concentrate the analysis of the essentially graphic characteristics of the scribble and guarantees the possibility of comparisons, both with reference to the execution modes inside the same scribble, and regarding comparisons among the various scribbles.

Still for the ease of automation, the line acquired by the electronic processor is equipped with information regarding sex and age or the age range of the persons who has drawn it.

The sensible area of the digital support is divided in various zones of different significance, preferably in four identical squares.

The digital support is able to communicate to the electronic processor the quantitative characteristics of the line, particularly for every point of the line the spatial coordinates, the instant of detection, and preferably also the pressure applied to the sensitive area. On the base of such data, the electronic processor can also acquire in an derived way also the punctual and average speed and acceleration by executing the line, the total length of the line, the length of a portion of the line present in each quadrant, the initial and final point of the line, various averages and various indexes of dispersion, etc.

The electronic processor has finally memorizing means of the line also as an image and means for emitting a synthesis script of the profile coming from the analysis of the line, for instance a script in a multi-media form (graphic or written form and/or audio and/or video).

The method for the automation of the interpretative analysis of a digital line drawn by a person comprises some preliminary steps essentially dedicated to the prearrangement of a first neural supervised network and preferably also of a second neural supervised network.

In brief in a preliminary step, by means of the electronic digital support an archive of lines is built by detecting the data referring to digital lines drawn by a multitude of persons. The archive must be sufficiently wide in order to permit a correct and complete training of the neural networks.

In another preliminary step, the electronic processor acquires the graphic evaluations of each line of the archive.

In another preliminary step, the electronic processor acquires for each lie of the archive the psychological evaluations.

In another preliminary step, the first neural supervised network is trained to associate, for each line of the archive, the graphic evaluations to the corresponding psychological evaluations. The training of the first and/or second neural supervised network is therefore realized by providing for each single line of the archive, as an input the graphic evaluations and as an output the psychological evaluations.

The psychological evaluations can be established by an expert or acquired by means of another test.

In the examined case, in which as an example the first neural supervised network is trained to associate the graphic evaluations of each of the lines of the archive to psychological evaluations deriving from the analysis of each of the lines by the expert, another preliminary step is provided in order to provide a second supervised neural network with the corresponding training to associate the graphic evaluations to each of said lines of the archive to psychological evaluations deriving from the other test.

In this way the psychological evaluations, when a new line is drawn onto the digital electronic support, can be executed both from the first supervised neural network and from the second supervised neural network.

The graphic evaluations comprise graphic quantitative evaluations established by the electronic processor, and graphic formal/qualitative evaluations, which are at their turn divided in first graphic formal/qualitative evaluations established by the expert and second graphic formal/qualitative evaluations established by the pertaining of the lines to classes with similar characteristics self-generated from a neural no-supervised network.

There is another preliminary step of providing a third supervised neural network, which is trained to associate to each line of the archive the corresponding first graphic formal/qualitative evaluations established by the expert. The training of the third supervised neural network is therefore realized by inputting each line present in the archive and outputting the relative first graphic formal/qualitative evaluations established by the expert.

Also for this network it is possible to apply the methodology of extracting of rules.

In the preliminary steps were therefore trained the first neural supervised network, the second neural supervised network and the third neural supervised network and the non supervised network was preset.

The training of the first, second and third neural network can also be constantly updated and improved with other examples.

It must be noted that in order to perform the graphic evaluations of the lines classes of graphic quantitative characteristics indicated by the expert are established and deemed generally significant, of the classes of first graphic formal/qualitative characteristics also indicated by the expert and of the classes of second graphic formal/qualitative characteristics self-generated from the neural non supervised network conveniently addressed by using dimensions deemed significant.

Conversely, to perform the psychological evaluations of the lines, in the particular case examined in which they are established by the expert, it is once again he who will choose the classes of psychological characteristics.

After the training of the first, second and third neural supervised network and after having disposed the non supervised neural network, the method can be finally actuated for the interpretative completely automated analysis of a new line drawn on the digital electronic medium.

For the interpretative analysis of a new line, one proceeds also as follows.

The person draws a new line on the digital electronic medium which detects from it the data and sends them to the electronic processor.

The electronic processor processes automatically the graphic quantitative evaluations of the new line and from the non supervised network gets automatically the second graphic formal/qualitative evaluations of the new line, whereas the first graphic formal/qualitative evaluations, if deemed necessary, can be obtained automatically from the third neural network.

At this point the first or second supervised trained neural network associates automatically the graphic evaluations to the psychological evaluations.

Through the method of the invention it is therefore possible to automate the entire process of administration, execution, acquisition and evaluation of a continuous line freely drawn by the person on a digital medium in order to comply at the same time with the previously indicated needs concerning speed, independence from cultural factors and ability, no need of the presence of an administrator and of an expert, immediacy and easiness of administration and execution, and the needs of accuracy and coherence of psychological evaluation and possibility of further developments and researches.

Through the first or second supervised trained neural network it is possible to associate coherently different criteria of graphic evaluation (quantitative, formal and qualitative criteria) with criteria of psychological evaluation, to elaborate a highly personalized psychological profile of the person.

The prevision of graphic evaluations made according to different (quantitative, formal and qualitative) criteria permit to consider at the same time the particular precision of measurement and calculation of the electronic processor (for the graphic quantitative evaluations), of the evaluative richness and the experience of an expert person (for the graphic qualitative evaluations), of the logic formal coherence of a classificatory system self-generated by a neural non supervised network (for the graphic formal/qualitative evaluations).

Figure 8:
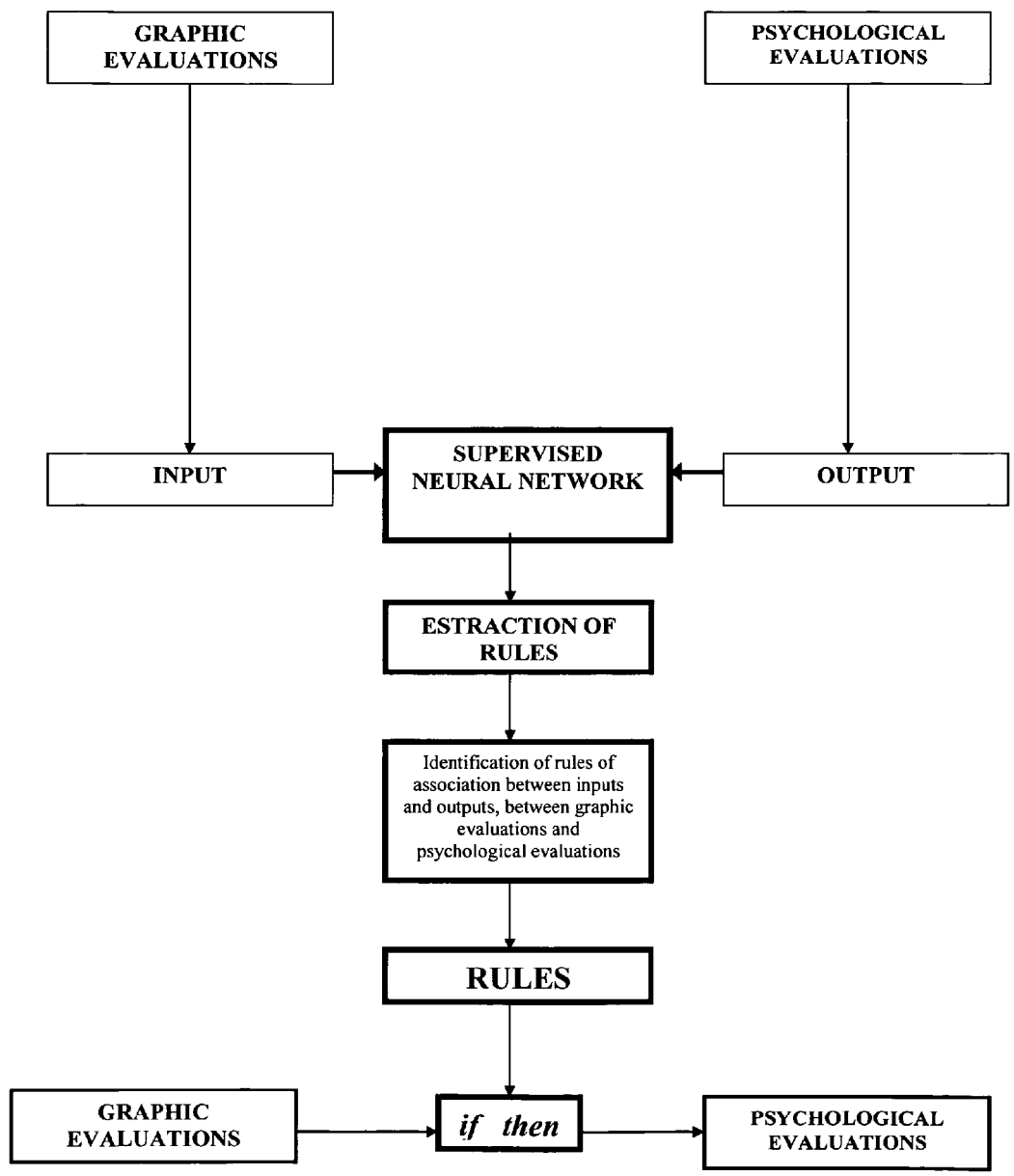
FIG. 8 shows a block diagram with the mode of extraction of the rules from said first and second trained supervised network.

By means of suitable algorithms are advantageously extracted from the neural networks the rules which permit to describe the knowledge acquired from the neural networks after they have been trained. In this way the knowledge of the networks and consequently the criteria of association among graphic evaluations and psychological evaluations, are made explicit with deductive rules of the king "IF" the circumstance "A" arises, "THEN" the circumstance "B" is presented (FIG. 8).

The aim of the extraction of rules is to make explicit the evaluative criteria of the neural networks in order to perform functions of control and progressive objectification of the criteria of evaluation, classification and association.

It is also advantageously possible to substitute the criteria of psychological evaluation of the expert with criteria of psychological evaluation deriving from any other test.

The aim of the substitution is not to make only comparisons among different modes of psychological evaluation (for instance for the validation of tests), but above all, to translate any other test in a test based on the graphic characteristics of a scribble, by benefiting from all the characteristics of this, for instance immediacy, easiness, automation.

Figure 3:
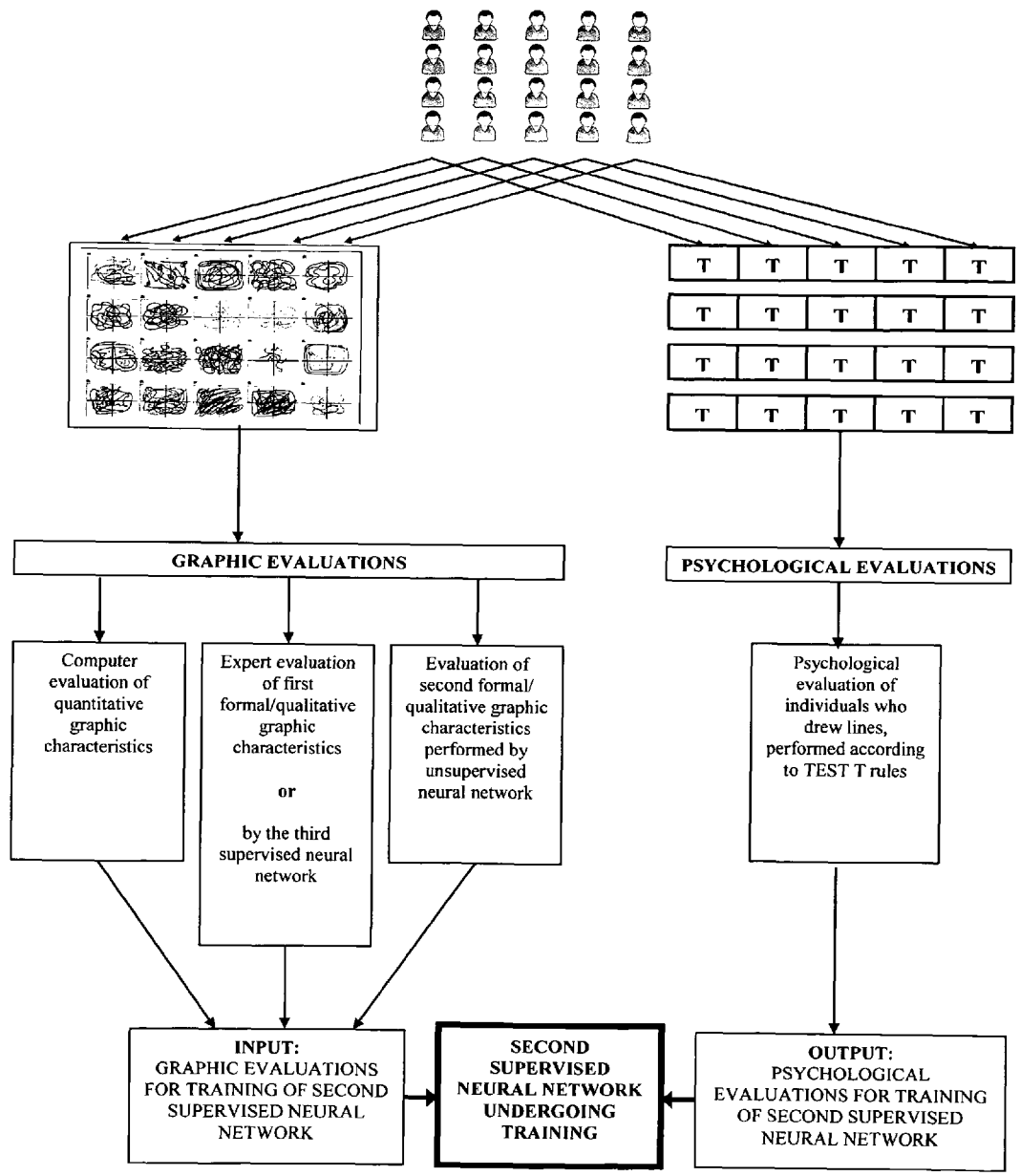
FIG. 3 shows a diagram with the training procedure of the second supervised neural network for the association of the graphic evaluations of said lines to psychological evaluations of said lines provided by another test.
Figure 4:
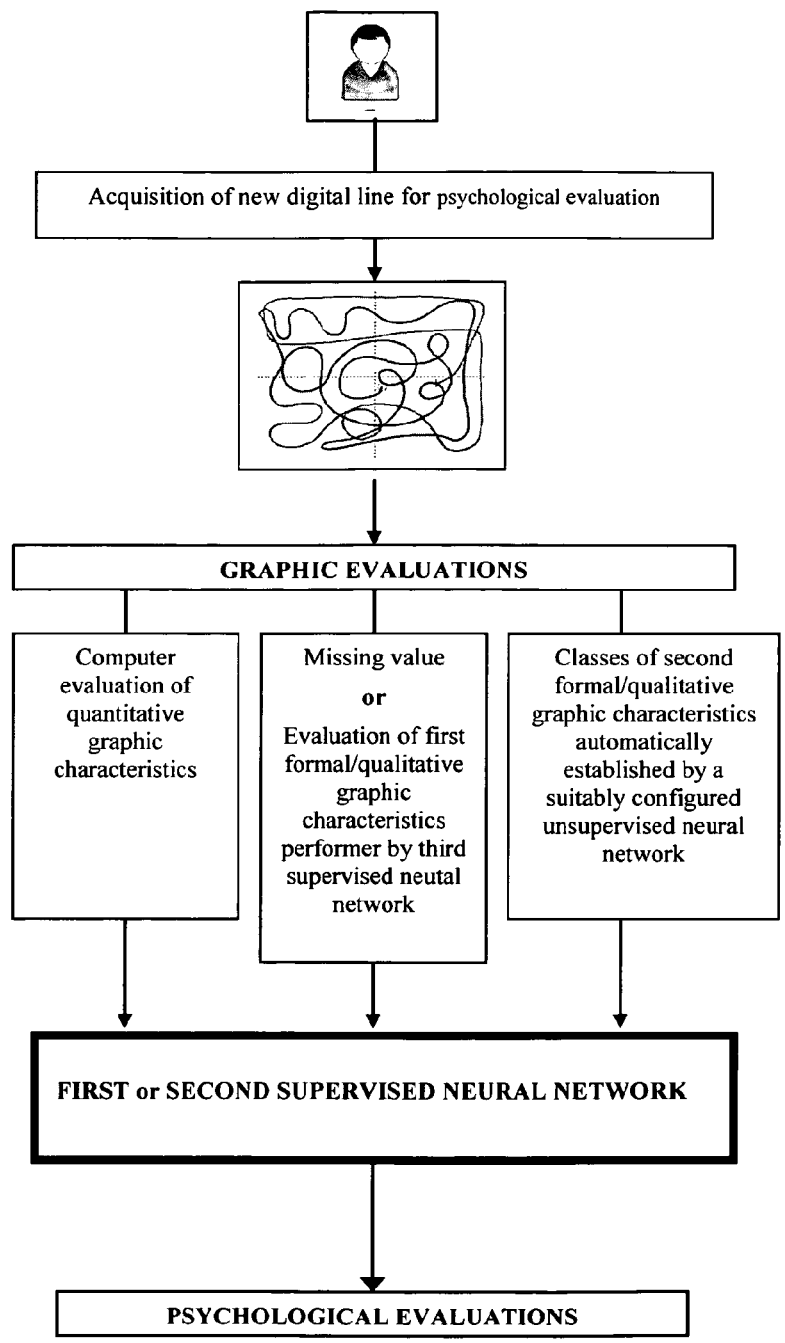
FIG. 4 shows a diagram explaining the interpretative analysis of a new line.
Figure 7:
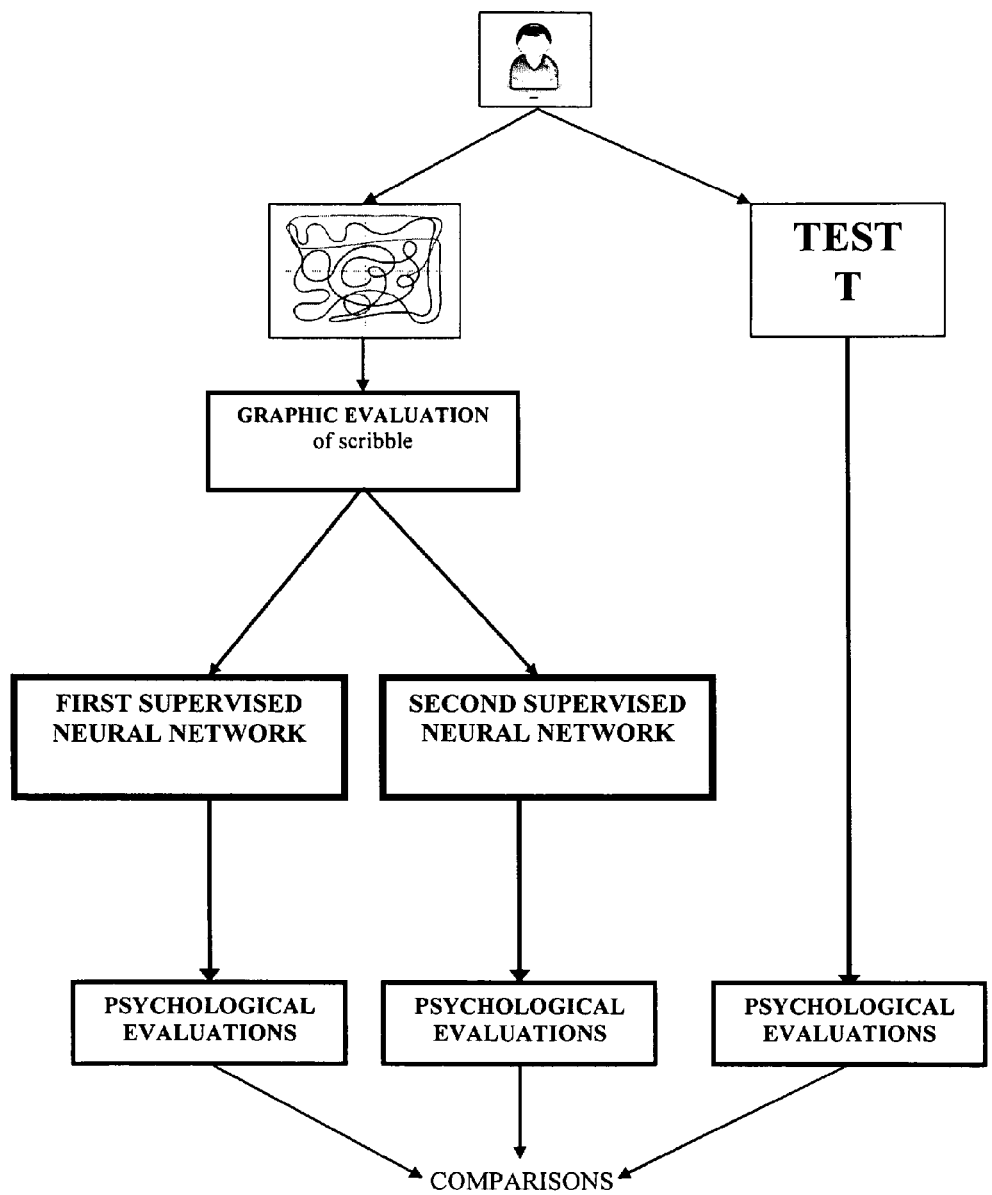
FIG. 7 shows the procedure for substituting the criterion of said psychological evaluations.

The substitution is realized by providing a second supervised neural network which is trained to associate the graphic evaluations no more to psychological evaluations of the expert but to the psychological evaluations deriving from another test (indicated with T in FIGS. 3 and 7).

Substantially one proceeds with a double acquisition. A suited number of persons (sufficiently great for the training of the neural networks) draw a line on the digital electronic medium and simultaneously perform also a second test indicated with T. The psychological evaluations of the test T are acquired through the modes referring to the specific test T.

At this point a second supervised neural network is provided, which is trained to associate, for each drawn line, the graphic evaluations to the psychological evaluations which derive from the test T.

It has to be noted that the presence of the expert can be no more necessary also for the graphic evaluations necessary for the training of the second supervised neural network, as the graphic formal/qualitative evaluations can be for instance substituted with the third supervised neural network trained as said previously.

Once having completed the training of the network, the psychological evaluations, when a new line is drawn on the digital electronic medium, can be executed from the first supervised neural network and the second supervised neural network and by executing the test T. Therefore three distinct psychological evaluations can be compared: those deriving from the first trained supervised neural network, those deriving from the second trained supervised neural network and those deriving directly from the test T.

If the psychological evaluations are substantially similar, then the three test are interchangeable.

Figure 5:
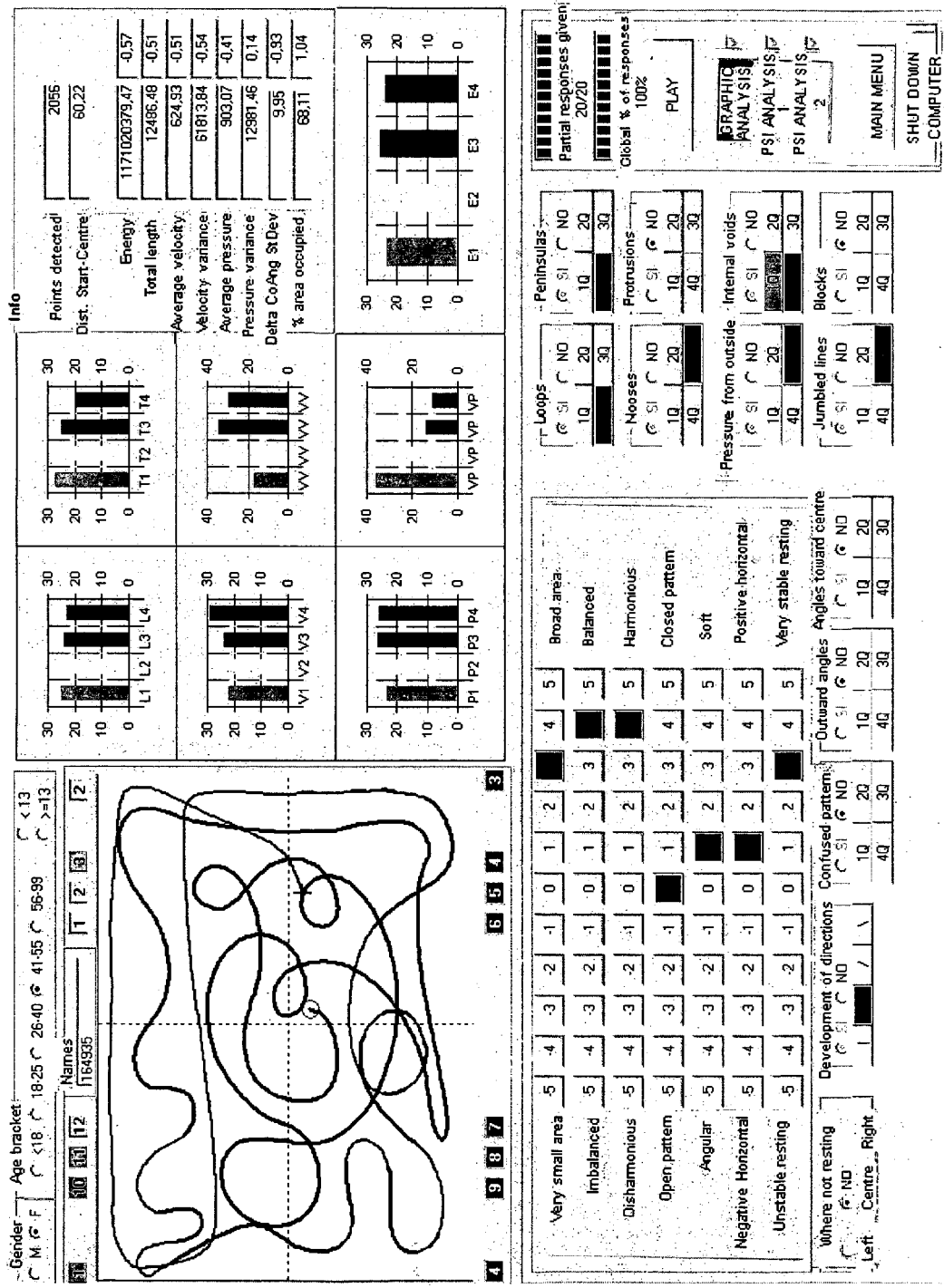
FIG. 5 shows the interface of the electronic processor which is presented to the expert for the first graphic formal/qualitative evaluations of said lines in the preliminary step for the acquisition of the graphic evaluations of each of said lines.

In FIGS. 5 and 6 the graphic and psychological characteristics considered are indicated in detail for the evaluations by the expert.

In FIG. 5 in the graphic interface which the electronic processor presents to the expert for the evaluation of the graphic formal/qualitative characteristics of the line, in a first sector of the interface an image is present of the line in the sensible area divided in the four quadrants, in a second sector of the interface the graphic quantitative evaluations of the line produced by the electronic processor, and in another sector a mask relative to the graphic formal/qualitative characteristics in which the graphic formal/qualitative evaluations must be inserted by the expert.

In particular, as the graphic quantitative characteristics are concerned, the electronic processor computes, for each drawn line, for instance the number of detected points, the distance of the initial point of the line from the center of the sensible area, the energy, the total length of the line, the average speed of execution, the variance (offset from the average of all analyzed lines) of the speed, the average pressure, the variance of the pressure and the occupied area. Such computations are made for each of the four quadrants in which the sensible area is divided.

As far as the first graphic formal/qualitative characteristics are concerned, for each line for instance are considered the harmony, the balance, the amplitude of the utilized area, the plasticity, the softness, the stability of support, the closure of the drawing, the horizontal positivity and the presence of some particular shapes as for instance slipknots, herniae, bundling, blocks, bends, peninsulae, inner voids.

The graphic formal/qualitative evaluations which the expert must insert through the mask present in the interface are related to a score in an interval (from −5 to +5) or they are of an exclusive yes/no kind. Such evaluations will be properly memorized by the electronic processor.

As far as the second graphic formal/qualitative characteristics are concerned, the non supervised neural network is predisposed in order to be able to make groupings, from it independently detected, with reference to similar formal/qualitative characteristics. For instance, a grouping of neurons could be activated when the drawing is balanced and has corners in determined areas.

In FIG. 6 in the graphic interface which the electronic processor presents to the expert for the evaluation of the psychological characteristics of the line, in a first sector of the interface an imagine is present of the line in the sensible area divided in the four quadrants, in a second sector of the interface the graphic quantitative evaluations of the line produced by the electronic processor, and in another sector a mask relative to the psychological characteristics in which the psychological evaluations must be inserted by the expert.

As far as the psychological characteristics are concerned, for each line in a first analysis are considered the masculinity, the introversion, the hystericism, the depression, the schizophrenia, the paranoia, the hypochondria, the sensibility, the melancholy, the sentimentalism, the problems with the father and the mother, the capacity of realization and perception, and in a second analysis the simple personality, the extroversion, the availability, the determination, the safety, the concreteness, the rationality, the defensive personality, the lack of ideality, the propensity to the transcendence, the aggressiveness, the nevroticism, the physicality issues, the rationalization issues.

The psychological evaluations which the expert must insert by means of the mask present in the interface are referred to a score within a range which can vary in function of the psychological characteristic (from −10 to +10, from 0 to +10, from −5 to +5), or they are of an exclusive yes/no kind. Such evaluations will be conveniently memorized by the electronic processor.

The so conceived method and the device for the automation of the interpretative analysis of a digital line drawn by a person are subject to numerous modifications and variations, all falling within the concept of the invention; furthermore, all details can be substituted with technically equivalent elements.

The invention claimed is:

1. A method for automation of the interpretative analysis of a digital line drawn by a person on a digital electronic medium, the method comprising:
   a preliminary step for the acquisition of an archive of digital lines drawn by a plurality of persons;
   a preliminary step for the acquisition of graphic evaluations of each of said lines of said archive;
   a preliminary step for the acquisition of psychological evaluations of the persons who drew each of said lines of said archive;
   a preliminary step of providing a at least a supervised neural network and relative training to associate, for each of said lines of said archive, the graphic evaluations with the corresponding psychological evaluations;
   a step for the acquisition, through said digital medium, of a new digital line drawn by a person for the performance of its interpretative analysis, wherein said digital line comprises a scribble drawn on a sensitive area of said digital medium for a determined time and without detachment from the sensitive area, wherein the acquisition of said new digital line includes both the graphic result of the scribble and the dynamics with which it is executed, and wherein only the sex and age/age range of the person who has drawn said digital line is associated with said digital line;
   a step for the acquisition of the graphic evaluations of said new line, wherein said graphic evaluations of each of said lines of said archive comprise at least quantitative graphic evaluations established by an electronic processor interacting with said digital medium and formal/qualitative graphic evaluations; and
   an association step wherein said supervised neural network automatically associates the corresponding psychological evaluations with the graphic evaluations of said new line.

2. The method for automation of the interpretative analysis of a digital line drawn by a person according to claim 1, wherein in said preliminary step for the acquisition of psychological evaluations of the persons who drew each of said lines of said archive, said psychological evaluations are established by an expert or acquired through the performance of a further test.

3. The method for automation of the interpretative analysis of a digital line drawn by a person according to claim 1, wherein said supervised neural network is trained to associate the graphic evaluations of each of said lines of said archive with psychological evaluations deriving from the analysis of each of an lines by said expert.

4. The method for automation of the interpretative analysis of a digital line drawn by a person according to claim 1, wherein said supervised neural network is a first supervised neural network, and further comprises a second supervised neural network that is trained to associate the graphic evaluations of each of said lines of said archive with psychological evaluations deriving from another test.

5. The method for automation of the interpretative analysis of a digital line drawn by a person according to claim 4, further comprising a step for the performance of psychological evaluations both by said first supervised neural network and by said second supervised neural network when said new line is drawn on said digital electronic medium.

6. The method for automation of the interpretative analysis of a digital line drawn by a person according to claim 4, further comprising a preliminary step of providing a third supervised neural network and relative training to associate the corresponding first formal/qualitative graphic evaluations with each of said lines of said archive.

7. The method for automation of the interpretative analysis of a digital line drawn by a person according to claim 6, wherein said third supervised neural network automatically associates the corresponding first formal/qualitative graphic evaluations with said new line.

8. The method for automation of the interpretative analysis of a digital line drawn by a person according to claim 6, further comprising a step for the extraction of general rules for association of the evaluations from said first and/or second and/or third trained neural networks.

9. The method for automation of the interpretative analysis of a digital line drawn by a person according to claim 1, wherein said formal/qualitative graphic evaluations of each of said lines of said archive in said preliminary step for the acquisition of graphic evaluations comprise first formal/qualitative evaluations established by an expert.

10. The method for automation of the interpretative analysis of a digital line drawn by a person according to claim 1, wherein the formal/qualitative graphic evaluations of each of said lines of said archive in said preliminary step for the acquisition of graphic evaluations comprises second formal/qualitative evaluations based on belonging to classes with similar formal/qualitative evaluations self-generated by a non-supervised neural network.

11. The method for automation of the interpretative analysis of a digital line drawn by a person according to claim 1, wherein said quantitative graphic evaluations refer to quantitative characteristics comprising at least geometric, physical and statistical parameters of said lines.

12. The method for automation of the interpretative analysis of a digital line drawn by a person according to claim 11, wherein said physical parameters of said quantitative characteristics comprise, for each point detected during drawing, at least the spatial position thereof on the sensitive area of the digital electronic medium, the instant in which it was performed and the pressure with which it was performed.

13. A device for the automation of interpretative analysis of a digital line drawn by a person comprising an electronic processor and a digital electronic medium that interacts with the electronic processor for the detection of the digital line, the electronic processor having a computer readable medium having computer-executable instructions that when executed implement a method stored on the processor for performance of a method comprising
   a preliminary step for the acquisition of an archive of digital lines drawn by a plurality of persons;
   a preliminary step for the acquisition of graphic evaluations of each of said lines of said archive;
   a preliminary step for the acquisition of psychological evaluations of the persons who drew each of said lines of said archive;
   a preliminary step of providing a first-supervised neural network and relative training to associate, for each of said lines of said archive, the graphic evaluations with the corresponding psychological evaluations;
   a step for the acquisition, through said digital medium, of a new digital line drawn by a person for the performance of its interpretative analysis, wherein said digital line comprises a scribble drawn on a sensitive area of said digital medium for a determined time and without detachment from the sensitive area, wherein the acquisition of said new digital line includes both the graphic result of the scribble and the dynamics with which it is executed, and wherein only the sex and age/age range of the person who has drawn said digital line is associated with said digital line;

a step for the acquisition of the graphic evaluations of said new line, wherein said graphic evaluations of each of said lines of said archive comprise at least quantitative graphic evaluations established by an electronic processor interacting with said digital medium and formal/qualitative graphic evaluations; and an association step wherein said at least supervised neural network automatically associates the corresponding psychological evaluations with the graphic evaluations of said new line, wherein the digital electronic medium is a graphics tablet or a touch screen.

\* \* \* \* \*